US00PP18291P3

(12) United States Plant Patent
NeSmith et al.

(10) Patent No.: US PP18,291 P3
(45) Date of Patent: Dec. 11, 2007

(54) RABBITEYE BLUEBERRY PLANT NAMED 'VERNON'

(50) Latin Name: *Vaccinium ashei*
Varietal Denomination: Vernon

(75) Inventors: D. Scott NeSmith, Molena, GA (US); Arlen D. Draper, Payson, AZ (US)

(73) Assignees: University of Georgia Research Foundation, Inc., Athens, GA (US); The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 11/261,408

(22) Filed: Oct. 28, 2005

(65) Prior Publication Data

US 2007/0101469 P1 May 3, 2007

(51) Int. Cl.
*A01H 5/00* (2006.01)

(52) U.S. Cl. ..... Plt./157

(58) Field of Classification Search ..... Plt./157
See application file for complete search history.

(56) References Cited

PUBLICATIONS

NeSmith et al.; 'Vernon': A New Early Season Rabbiteye Blueberry Cultivar; Hort Science 40(3): p. 886; Jun. 2005; 65th Annual Meeting of the Southern Region of the American–Society for Horticultural Science; Dialog Printout.*

* cited by examiner

*Primary Examiner*—Kent L. Bell
(74) *Attorney, Agent, or Firm*—Greenlee Winner and Sullivan, PC

(57) ABSTRACT

The most distinctive feature of the rabbiteye blueberry, 'Vernon', is its combination of late bloom/early ripening, favorable commercial fruit attributes, high and consistent yield, excellent plant vigor, and large berry size.

4 Drawing Sheets

ACKNOWLEDGMENT OF FEDERAL RESEARCH SUPPORT

The invention was made with government support under the Hatch Act. The government has certain rights in the invention.

Botanical classification: *Vaccinium ashei* Reade.

Varietal denomination: 'Vernon'.

BACKGROUND OF THE INVENTION

The fruit of the plant is primarily used as fresh fruit for shipping. Also suitable for customer-pick and processing markets.

'Vernon' was selected in 1990 at the Coastal Plain Experiment Station in Tifton, Ga. from a cross of T-23×T-260. T-23 was the female parent and T-260 was the male parent. T-23 is a progeny from a cross of W4×Callaway, and T-260 is from a cross of Brightwell×T-139. W4 is a wild type selection, and T-23, T-260 and T-139 are breeding lines developed, but not released, at the University of Georgia. T-23 and T-260 are older breeding lines no longer in existence. These were never released or otherwise utilized due to inferior fruit color, size, and/or quality. None of the lines used to produce this selection are patented. 'Vernon' has been tested in plantings at Alapaha Ga., Griffin Ga., Blairsville Ga., Clarksville Ark. and Poplarville Miss. since 2001. The resulting data from 10-site/years indicate that the new variety is widely adapted to areas conductive to rabbiteye blueberry production.

'Vernon' has been asexually propagated on many occasions since 1995 by softwood cuttings at Griffin Ga. It roots readily from softwood cuttings and in all cases the clones propagated from cuttings have maintained the vegetative and fruit characteristics of the original selection.

'Vernon' has been primarily compared with the current, early rabbiteye industry standards 'Climax' (non patented), and 'Premier' (non patented). In Georgia, 'Climax' yields have been highly unreliable, it is subject to spring freeze damage due to early blooming, and 'Premier' yields have been only moderate.

In tests over several years at Alapaha, Ga., 'Vernon' yielded significantly more than 'Climax' in 4 out of 6 years, and significantly more than 'Premier' in 2 out of 4 years. On average over a 6-year period, 'Vernon' produced 12.8 lb/bush, 86% more than 'Climax' (6.8 lb/bush) and 29% more than 'Premier' (9.9 lb/blush). Over a 2-year period at Griffin and Blairsville, Ga., 'Vernon' yielded 83% more than 'Climax' on average.

Over a 5-year period in Alapaha, Ga., 'Vernon' flowering time was 10 days later than 'Climax' on average, and was 5 days later than 'Premier'. However, 'Vernon' ripened at a similar time to both 'Premier' and 'Climax'. Thus, flowering time for 'Vernon' is late enough to provide some protection from frost problems, and ripening time is early enough to receive higher early market prices.

In addition to good yields and a favorable flowering time, 'Vernon' plant vigor and berry characteristics have been equal to or greater than 'Climax' and 'Premier' over a 5-year rating period at Alapaha, Ga. Berry size has been particularly favorable, which is desirable for growers. The larger berry size of 'Vernon' (1.87 g average) as compared to 'Climax' (1.27 g average), more readily facilitates hand-picking, and produces a better fruit pack-out. 'Vernon', with a rating of 8.5 on a 1 to 10 scale, is firmer than 'Premier' (7.4), which is important for maintaining quality during harvesting and handling.

As for adaptability to other areas, 'Vernon' seems to be as adaptable as 'Climax'. Fruit and plant characteristics of 'Vernon' and 'Climax' were evaluated for 2 to 4 year-old plants at 2 locations in Georgia, one location is Mississippi, and one location in Arkansas during 2003. The two cultivars generally ripened at the same time, and had similar berry scar, color, firmness, and flavor. However, 'Vernon' had larger berry size (2.06 g average) than 'Climax' (1.56 g average), and typically had better overall plant vigor.

The new variety 'Vernon' is self fertile to a degree; however, it is recommended that it be planted with another rabbiteye cultivar with a similar bloom time for cross pollination. The recent release 'Alapaha' (U.S. patent application Ser. No. 10/225,211, issued on Feb. 21, 2006 as U.S. Plant Pat. No. 16,266) would be a good choice for planting with the new variety.

SUMMARY OF THE INVENTION

Description and specification of a new and distinct rabbiteye blueberry named 'Vernon' which originated from seed produced by a hand-pollinated cross of T-23 and T-260 is provided. The new 'Vernon' variety can be distinguished from the early rabbiteye varieties currently available for blueberry production in Georgia by its late bloom/early ripening, with subsequent short fruit development period, its high and consistent productivity, moderate chill requirement, large berry size and its high quality fruit suitable for mechanical harvesting for the fresh market.

BOTANICAL DESCRIPTION OF THE PLANT

Figure 1:
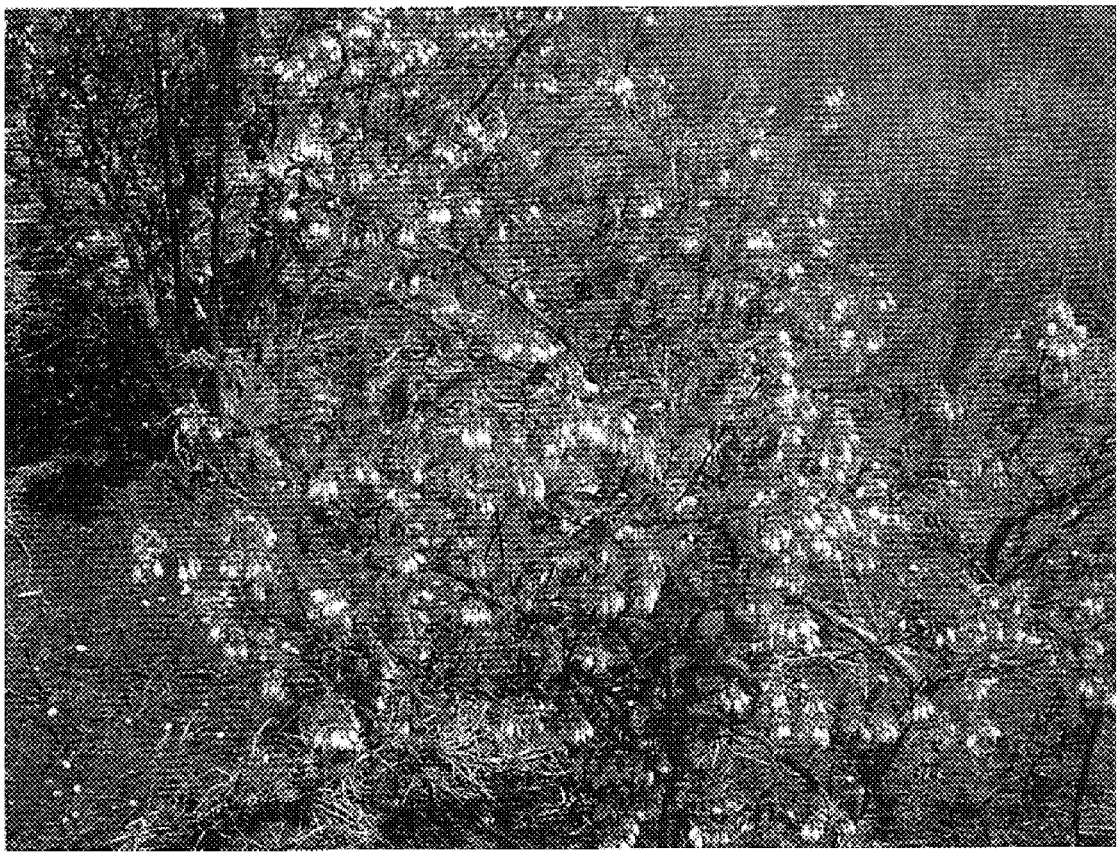
FIG. 1. shows a 4-year old plant during flowering.
Figure 2:
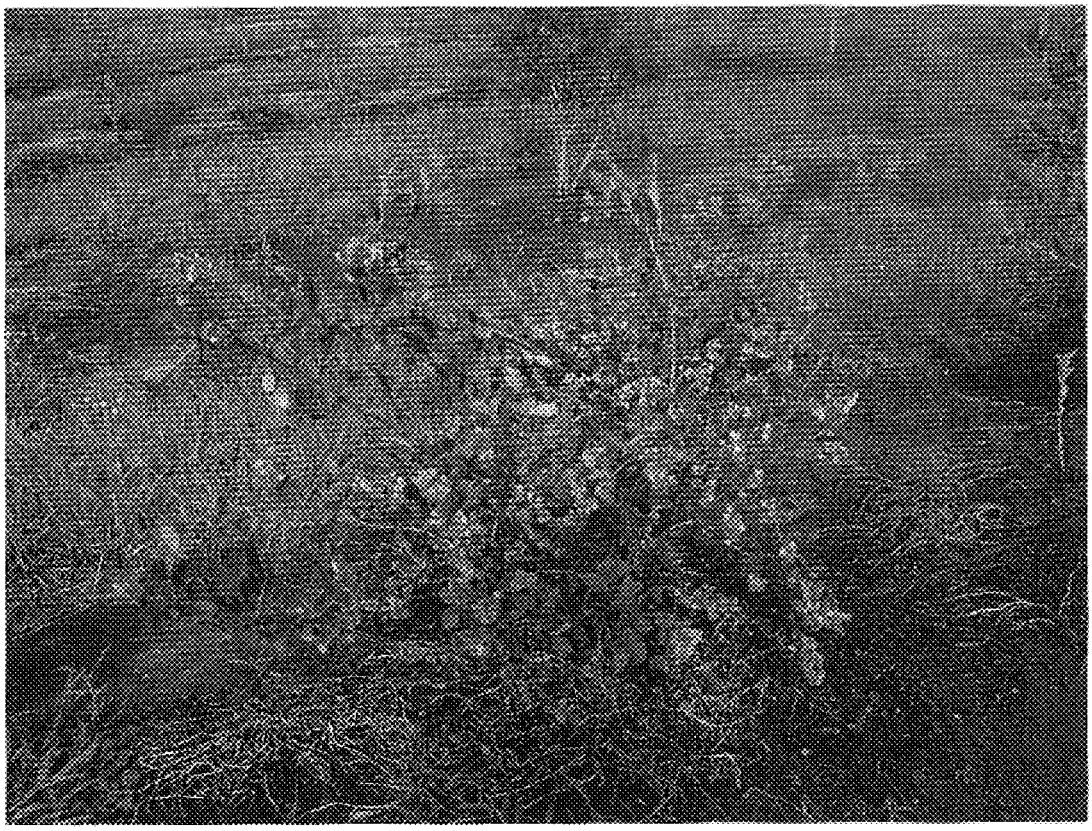
FIG. 2. shows a 4 year old plant during berry opening.
Figure 3:
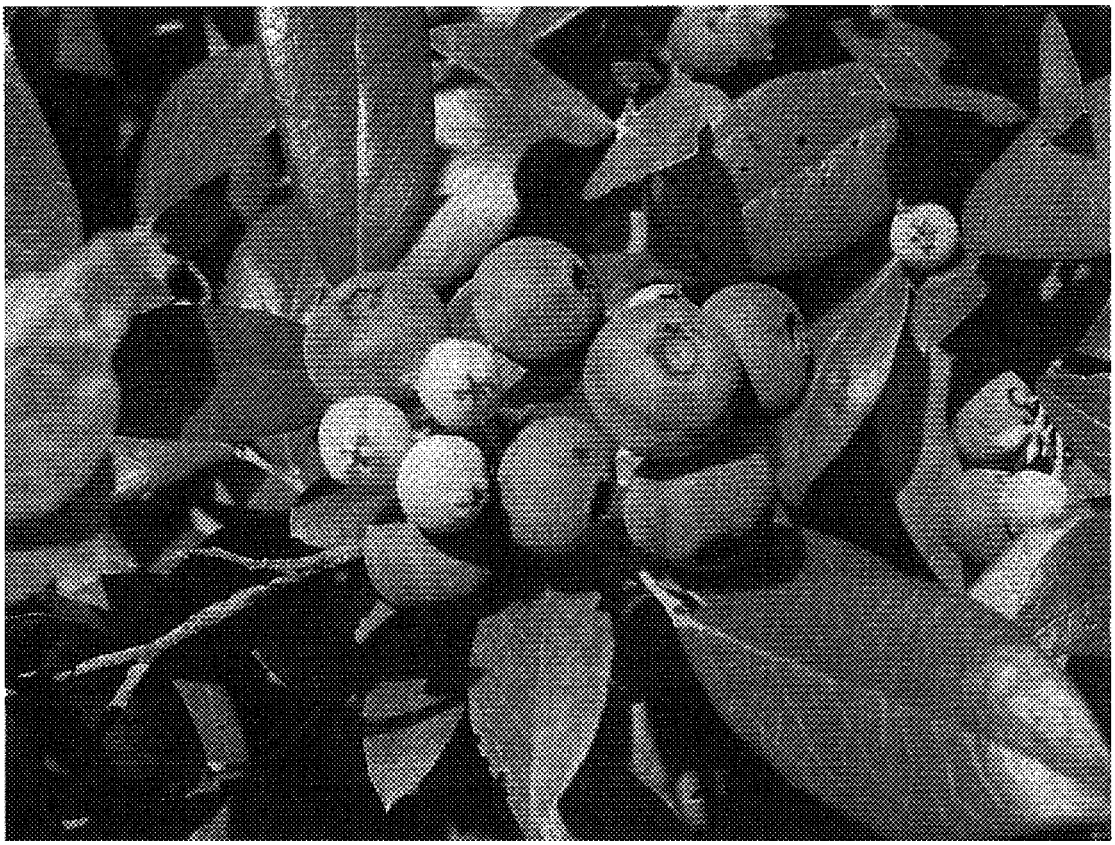
FIG. 3. shows a ripe fruit cluster.
Figure 4:
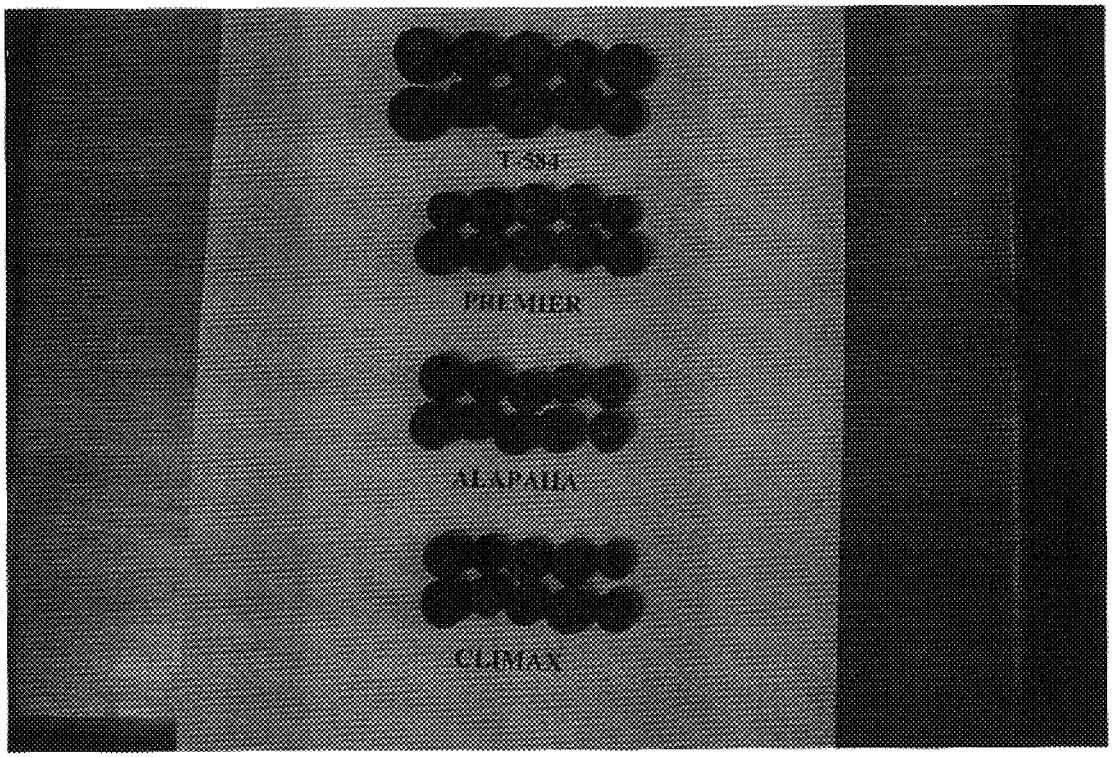
FIG. 4. shows berries of 'Vernon' (T-584) compared to berries of 'Premier', 'Alapaha' and 'Climax'.

The following is a detailed description of the botanical and pomological characteristics of 'Vernon'. Where dimensions, sizes, colors, and other characteristics are given, it is to be understood that such characteristics are approximations and averages set forth as accurately as practicable. Color data are presented in The Royal Horticultural Society Colour Chart designations. The descriptions reported herein are largely from 4 year old plants grown in Griffin, Ga., with supplemental irrigation.

Plant:

*Size.*—Reaches 1.5 m or more in height in 4 years. Three to four year old plants have a plant spread of 25–40 cm near base and 100–150 cm near top of plant.

*Growth habit.*—Upright, numerous canes.

*Growth.*—Vigorous shoot growth. Produces abundant canes from the base (4 to 8), but not strongly suckering.

*Productivity.*—Highly productive, concentrated ripening, good yield consistency from year to year, averaging 12.8 lb per bush per year over a five year period from 1998–2003 from plants established in 1992, grown without mulch, bedding, or irrigation at Alapaha, Ga.

*Cold hardiness.*—Plants should survive in USDA hardiness zones 6 thru 9.

*Chilling requirement.*—Plants require 500 to 550 hours of temperatures at or below 7° C. to induce normal leafing and flowering during the spring.

*Leafing.*—Plants readily break numerous leaf buds simultaneously with anthesis.

*Canes.*—Main cane base diameter 15–20 mm, color Greyed-Green (197D); first major branch diameter 8–10 mm, color Greyed-Green (197D); 2 year old cane diameter 9–12 mm, color Greyed-Orange (163B); current season wood diameter 2–6 mm, color Green (138B) and Yellow-Green (146C).

*Fruiting wood.*—Numerous shoots 10–15 cm in length, with internode lengths of 12–18 mm common.

Foliage:

*Leaf color.*—Healthy mature leaves; top side of leaf color is Green (137A), under side of leaf color is Yellow-Green (148C).

*Leaf surface.*—Glaucous (waxy).

*Leaf arrangement.*—Alternate, simple.

*Leaf shape.*—Elliptic.

*Leaf margins.*—Crenulate. Margins slightly ciliate, occasional stalked glands along leaf margin.

*Leaf venation.*—Pinnate with slight netting (or slightly reticulated).

*Leaf apices.*—Narrow acuminate.

*Leaf bases.*—Narrow cuneate to acute.

*Leaf dimensions.*—Length 60 to 65 mm; width 22 to 25 mm.

*Petioles.*—Small, 2 to 3 mm long. Color is Yellow-Green (145B). Petiole width is 1.3–1.5 mm.

Flowers:

*Date of* 50% *anthesis.*—March 17 (5 year average at Alapaha, Ga.).

*Flower shape.*—Urceolate.

*Flower bud number.*—High.

*Flowers per cluster.*—7 to 10.

*Flower fragrance.*—No.

*Corolla color.*—Green-White (157C.).

*Corolla length.*—8.0 to 9.0 mm.

*Corolla width.*—5.5 to 5.8 mm.

*Corolla aperture width.*—1.8 to 2.2 mm.

*Flower peduncle.*—Length 10 to 15 mm; Color Green (139C).

*Flower pedicel.*—Length 5 to 7 mm; Color Green (138A).

*Calyx* (*with sepals*).—Diameter 5.0 mm; color Green (137B).

*Stamen.*—Length 8.0 to 8.5 mm; number per flower 10; filament color: Yellow-Green (145D).

*Style.*—Length 9.5 to 10.0 mm; color Yellow-Green (146D).

*Pistil.*—Length 12.0 to 12.5 mm; ovary color Green (137C).

*Anther.*—Length 4.0 to 4.5 mm; number 10; color Greyed-Orange (172C).

*Pollen.*—Abundance: medium: color Yellow (8C). The cultivar has a moderate degree of self-compatibility.

Fruit:

*Date of* 50% *maturity.*—May 31$^{st}$ (5 year average at Alapaha, Ga.). Date of 10% maturity is May 21$^{st}$ and date of 90% maturity is June 10$^{th}$ on average.

*Fruit development period.*—75 days (5 year average at Alapaha, Ga.).

*Berry color.*—with wax Violet-Blue (97C); with wax removed Black (202A).

*Berry surface wax abundance.*—High.

*Berry Flesh Color.*—Green — White (157B).

*Berry weight.*—1st harvest 1.7 g to 1.9 g; $2^{nd}$ harvest 1.4 g to 1.7 g.

*Berry size.*—Height from calyx to scar 12.5 to 13.5 mm; diameter 16.0 to 18.0 mm.

*Berry shape.*—Semi-spherical.

*Fruit stem scar.*—Small to medium, dry, no tearing.

*Berry firmness.*—Firm to very firm (firmer than the cultivar 'Premier').

*Berry flavor and texture.*—Flavor good to excellent; good texture; not seedy.

*Storage quality.*—Good to very good.

*Suitability for mechanical harvesting.*—Suitable.

*Uses.*—Can be used as fresh fruit for shipping, for customer-pick and processing markets.

Seed:

*Seed abundance in fruit.*—Medium.

*Seed color.*—Greyed-Orange (165B).

*Seed dry weight.*—54.4 mg per 100 seed (air dry).

*Seed size.*—1.5 to 2.0 mm long.

We claim:

1. A new and distinct variety of rabbiteye blueberry plant, substantially as illustrated and described.

* * * * *